(12) United States Patent
Kageyama et al.

(10) Patent No.: US 9,862,225 B2
(45) Date of Patent: Jan. 9, 2018

(54) LIQUID APPLYING TOOL

(71) Applicant: KOTOBUKI & CO., LTD, Saitama (JP)

(72) Inventors: Hidehei Kageyama, Saitama (JP); Yoshio Noguchi, Saitama (JP); Sachio Arai, Saitama (JP)

(73) Assignee: KOTOBUKI & CO., LTD., Saitama (JP)

( * ) Notice: Subject to any disclaimer, the term of this patent is extended or adjusted under 35 U.S.C. 154(b) by 38 days.

(21) Appl. No.: 14/892,107

(22) PCT Filed: Jul. 31, 2014

(86) PCT No.: PCT/JP2014/070799
§ 371 (c)(1),
(2) Date: Nov. 18, 2015

(87) PCT Pub. No.: WO2015/020119
PCT Pub. Date: Feb. 12, 2015

(65) Prior Publication Data
US 2016/0136993 A1    May 19, 2016

(30) Foreign Application Priority Data

Aug. 6, 2013    (JP) ................. 2013-163564

(51) Int. Cl.
*B65H 37/00*    (2006.01)
*A45D 40/00*    (2006.01)
(Continued)

(52) U.S. Cl.
CPC ............... *B43K 7/03* (2013.01); *A45D 34/04* (2013.01); *A45D 40/20* (2013.01); *B43K 8/006* (2013.01);
(Continued)

(58) Field of Classification Search
CPC combination set(s) only.
See application file for complete search history.

(56) References Cited

U.S. PATENT DOCUMENTS 1,922,831 A * 8/1933 Vivian .................... B43K 5/04
  24/11 F
2,142,533 A * 1/1939 Stenersen ................ B43K 5/00
  401/154
(Continued)

FOREIGN PATENT DOCUMENTS

CN    101001551 A    7/2007
DE    203 01 714 U1    5/2003
(Continued)

OTHER PUBLICATIONS

Extended European Search Report from the Munich Patent Office in European Application No. EP 14833762.9-1704 dated Apr. 26, 2017.
(Continued)

*Primary Examiner* — David Walczak
(74) *Attorney, Agent, or Firm* — The Marbury Law Group, PLLC

(57) ABSTRACT

A liquid applying tool which can create pressurizing action with a simple structure and without any labor at the time of using the liquid applying tool, and allows liquid to be smoothly fed to a tip end of a liquid applicator member with the assistance of the pressurizing action.

7 Claims, 13 Drawing Sheets

(51) Int. Cl.
| | |
|---|---|
| *B43M 11/06* | (2006.01) |
| *A45D 34/04* | (2006.01) |
| *B43K 7/03* | (2006.01) |
| *B05C 17/00* | (2006.01) |
| *A45D 40/20* | (2006.01) |
| *B43K 23/12* | (2006.01) |
| *B43K 8/00* | (2006.01) |
| *B43K 8/04* | (2006.01) |
| *B43K 8/14* | (2006.01) |
| *B43K 8/18* | (2006.01) |

(52) U.S. Cl.
CPC .............. *B43K 8/04* (2013.01); *B43K 8/143* (2013.01); *B43K 8/18* (2013.01); *B43K 23/12* (2013.01); *B43M 11/06* (2013.01); *B65H 37/00* (2013.01); *A45D 2200/055* (2013.01); *B05C 17/00* (2013.01)

(56) References Cited

U.S. PATENT DOCUMENTS

| | | |
|---|---|---|
| 2007/0158372 A1 | 7/2007 | Kurek et al. |
| 2007/0172307 A1 | 7/2007 | Jo |

FOREIGN PATENT DOCUMENTS

| | | |
|---|---|---|
| EP | 2 933 117 A1 | 10/2015 |
| JP | 08108126 A | 4/1996 |
| JP | 2001270288 A | 10/2001 |

OTHER PUBLICATIONS

International Search Report from the Japanese Patent Office, International Application No. PCT/JP2014/070799 dated Oct. 14, 2014.
Chinese First Office Action issued for Application No. 201480044588.9 dated Nov. 1, 2016.

* cited by examiner

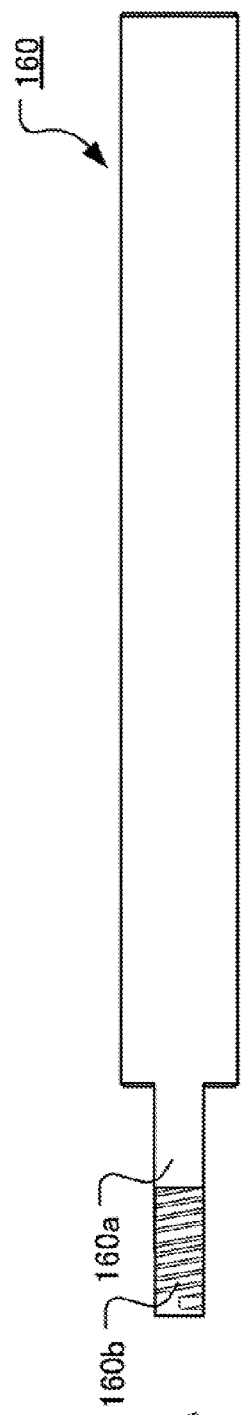
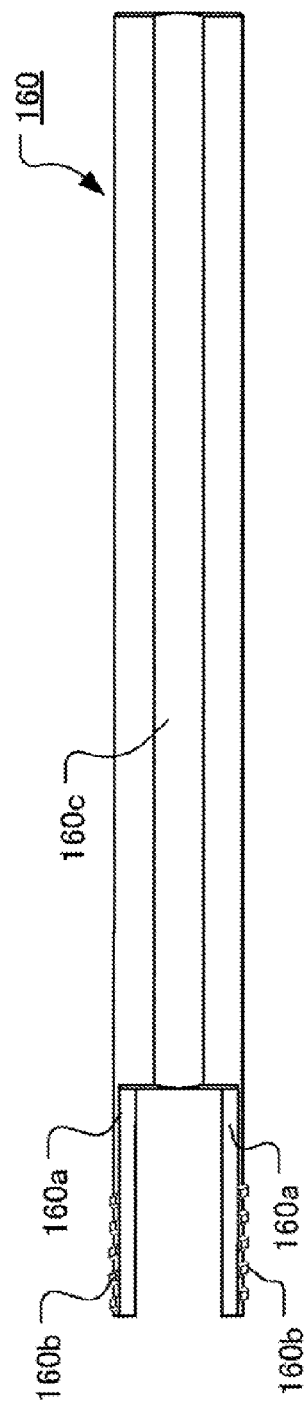

LIQUID APPLYING TOOL

FIELD OF INVENTION

The present invention relates to a liquid applying tool for applying liquid and, more particularly, to a liquid applying tool in which liquid in a liquid storage container of the liquid applying tool can be smoothly supplied to a tip end of a liquid applicator member of the liquid applying tool with the assistance of pressurizing action.

BACKGROUND ART

In the past, as a liquid applying tool, there has been known a liquid applying tool in which a tip end of a liquid applicator member housed in a tubular shaft of the liquid applying tool is adapted to be projected out of and retracted in the tubular shaft via a tip end opening of the tubular shaft by means of a rotary cam mechanism. The rotary cam mechanism generally includes a rotary cam member provided in the tubular shaft so as to be movable between an advanced position and a backward position, and a cam body formed around an inner peripheral surface of the tubular shaft. The rotary cam mechanism is adapted to be actuated by a knocking member inserted, via a rear end opening of the tubular shaft, in the tubular shaft with a rear end portion thereof being projected rearward from the rear end opening of the tubular shaft. Every time the rotary cam member is pushed by the knocking member, the rotary cam member is rotated by a predetermined angle with respect to the cam body and can be switched between the advanced position and the backward position. When the rotary cam member is located at the advanced position, the tip end of the liquid applicator member is projected out of the tip end opening of the tubular shaft. When the rotary cam member is located at the backward position, the tip end of the liquid applicator member is retracted in the tubular shaft.

For example, Patent Literature 1 proposes a structure which enables liquid in a liquid accommodating tube to be smoothly supplied to a liquid applicator member of a liquid applying tool by pressurizing action which is linked to the operation of a rotary cam mechanism. The liquid applying tool disclosed in the Patent Literature 1 includes a tubular shaft, a liquid accommodating tube movably inserted in the tubular shaft, a rotary cam mechanism for causing the liquid accommodating tube to be moved forward and rearward, a pressurization space defined in the tubular shaft and communicating with an interior of the liquid accommodating tube, and a pusher member (knocking member). In the liquid applying tool, when knocking force is applied to the pusher member to thereby cause the pusher member to be moved forward, a piston which is connected to the pusher member is moved forward and a rotary cam member of the rotary cam mechanism is moved forward to thereby cause the liquid accommodating tube to be moved forward. As the piston is moved forward, it tightly closes the pressurization space to thereby pressurize the pressurization space. Even after the pusher member is released from the knocking force, the piston is adapted to be maintained in the forward position, whereby the pressurization space is maintained in the pressurized state. Thereby, the interior of the liquid accommodating tube which communicates with the pressurization space is pressurized, and liquid accommodated in the liquid accommodating tube can be smoothly supplied to the liquid applicator member with the assistance of the pressurizing action.

However, in the above-mentioned liquid applying tool, a structure which causes the operation of the rotary cam mechanism and the pressurizing action to be linked to each other is required. Therefore, there is a problem that the structure of the liquid applying tool is made complicated.

Moreover, a ballpoint pen having a pressurizing pump mechanism provided in a tubular shaft thereof is disclosed in Patent Literature 2, for example. The pressurizing pump mechanism includes a pressurization chamber communicating with an interior of a liquid accommodating tube inserted in the tubular shaft, an elastic body adapted to be pushed into the pressurizing chamber, a compression spring for causing the elastic body to be biased in a direction to be separated from the pressurizing chamber, and a pusher bar for causing the elastic body to be forcedly moved forward. The pusher bar is inserted in the tubular shaft so as to be partially projected rearward from a rear end opening of the tubular shaft. The ballpoint pen further includes a cap which has an inner ball provided therein and is removably fitted around a tip end portion of the tubular shaft. When the ballpoint pen is used, the cap is removed from the tip end portion of the tubular shaft and then fitted around a rear end portion of the tubular shaft. When the cap is fitted around the rear end portion of the tubular shaft, the inner ball provided in the cap operatively pushes the pusher bar of the pressurizing pump mechanism and maintains the pushed state of the pusher bar, so that the liquid accommodating tube is maintained in a pressurized state.

CITATION LIST

Patent Literature

Patent Literature 1: Japanese Patent Application Laid-Open Publication No. 2010-125715
Patent Literature 2: Japanese Patent Application Laid-Open Publication No. 2007-152745

SUMMARY OF INVENTION

Technical Problems

However, in the ballpoint pen disclosed in the Patent Literature 2, when writing is performed using the ballpoint pen, the cap must be removed from the tip end portion of the tubular shaft and then fitted around the rear end portion of the tubular shaft in order to push the pusher bar to pressurize the interior of the liquid accommodating tube. Therefore, if a failure in attaching the cap to the rear end portion of the tubular shaft occurs, the liquid accommodating tube is not pressurized. In addition to the operation of removing the cap from the tip end portion of the tubular shaft, the operation of attaching the cap to the rear end portion of the tubular shaft is separately required in this way in order to pressurize the liquid accommodating tube. Therefore, a problem arises that time-consuming labor is required at the time of using the ballpoint pen. Moreover, the pusher bar is partially projected rearward from the rear end portion of the tubular shaft, so that a visual appearance of the ballpoint pen is deteriorated. In addition, there is a possibility that the pusher bar will be accidentally pushed without attaching the cap to the rear end portion of the tubular shaft, to thereby unnecessarily pressurize the liquid accommodating tube.

The present invention has been made in view of the above-mentioned problems and the object of the present invention is to provide a liquid applying tool which can create pressurizing action with a simple structure and without any labor at the time of using the liquid applying tool, and enables liquid in a liquid storage container of the liquid applying tool to be smoothly supplied to a liquid applicator member of the liquid applying tool with the assistance of the pressurizing action.

Solution to Problems

In accordance with a first aspect of the present invention, there is provided a liquid applying tool which comprises a liquid storage container having liquid stored therein and a liquid applicator member provided at a tip end portion thereof for applying the liquid, an outer container, the liquid storage container being housed in the outer container with at least a tip end of the liquid applicator member thereof being exposed to an outside of the outer container, a cap removably attached to a tip end portion of the outer container so as to cover the tip end of the liquid applicator member, a compression member arranged at a rear end portion of the liquid storage container in the outer container, and a power transmitting member configured to be reciprocation-moved in an axial direction in the outer container according to attaching/detaching of the cap, whereby one of the compression member and the liquid storage container is reciprocation-moved relative to the other of the compression member and the liquid storage container in the axial direction.

According to a second aspect of the present invention, the power transmitting member is adapted to be moved forward in an axial direction in the outer container according to detaching of the cap from the outer container, and the compression member is adapted to be moved forward relative to the liquid storage container in the axial direction according to the forward movement of the power transmitting member, the power transmitting member is adapted to be moved rearward in the axial direction in the outer container according to attaching of the cap to the outer container, and the compression member is adapted to be moved rearward relative to the liquid storage container in the axial direction according to the rearward movement of the power transmitting member.

According to a third aspect of the present invention, the liquid applying tool includes a forward biasing member provided in the outer container for causing the compression member to be biased forward in the axial direction.

According to a fourth aspect of the present invention, the power transmitting member is adapted to be moved rearward in the axial direction in the outer container according to detaching of the cap from the outer container, and the liquid storage container is adapted to be moved rearward relative to the compression member in the axial direction according to the rearward movement of the power transmitting member, the power transmitting member is adapted to be moved forward in the axial direction in the outer container according to attaching of the cap to the outer container, and the liquid storage container is adapted to be moved forward relative to the compression member in the axial direction according to the forward movement of the power transmitting member.

According to a fifth aspect of the present invention, the liquid applying tool includes a rearward biasing member provided in the outer container for causing the liquid storage container to be biased rearward in the axial direction.

According to a sixth aspect of the present invention, the power transmitting member is arranged between an inner peripheral surface of the outer container and an outer peripheral surface of the liquid storage container.

According to a seventh aspect of the present invention, the liquid storage container is formed integrally with the power transmitting member.

Advantageous Effects of Invention

According to the present invention, when the cap is detached from the outer container at the time when the liquid applying tool is used, the compression member is moved with respect to the liquid storage container in a direction pressurizing an interior of the liquid storage container, by action of the power transmitting member. Thus, by the indispensable operation of removing the cap from the outer container which is performed at the time of the use of the liquid applying tool, pressure in the liquid storage container can be pressurized. Therefore, it is possible to create the pressurizing action with the simple construction and without any labor. With resort to the pressurizing action, the liquid can be smoothly fed to the tip end of the liquid applicator member.

Moreover, when the cap is attached to the outer container, the compression member is moved with respect to the liquid storage container in a direction opposite to a direction, in which the compression member pressurizes the liquid storage container, by the action of the power transmitting member. Thus, the pressure in the liquid storage container is returned to a state prior to the pressurized state, so that when the cap is again detached from the outer container, the pressurizing action can be securely created in the liquid storage container.

BRIEF DESCRIPTION OF THE DRAWINGS

FIG. 11(a) is a plane view of the power transmitting member of the second embodiment;

FIG. 11(b) is a side view of the power transmitting member of the second embodiment;

DETAILED DESCRIPTION OF THE EMBODIMENTS

Liquid applying tools according to embodiments of the present invention will be discussed hereinafter with reference to the drawings. Incidentally, in each of the liquid applying tools, a side on which a liquid applicator member is disposed shall be referred to as "a tip end side" and an opposite side shall be referred to as "a rear end side".

(First Embodiment)

Figure 1:
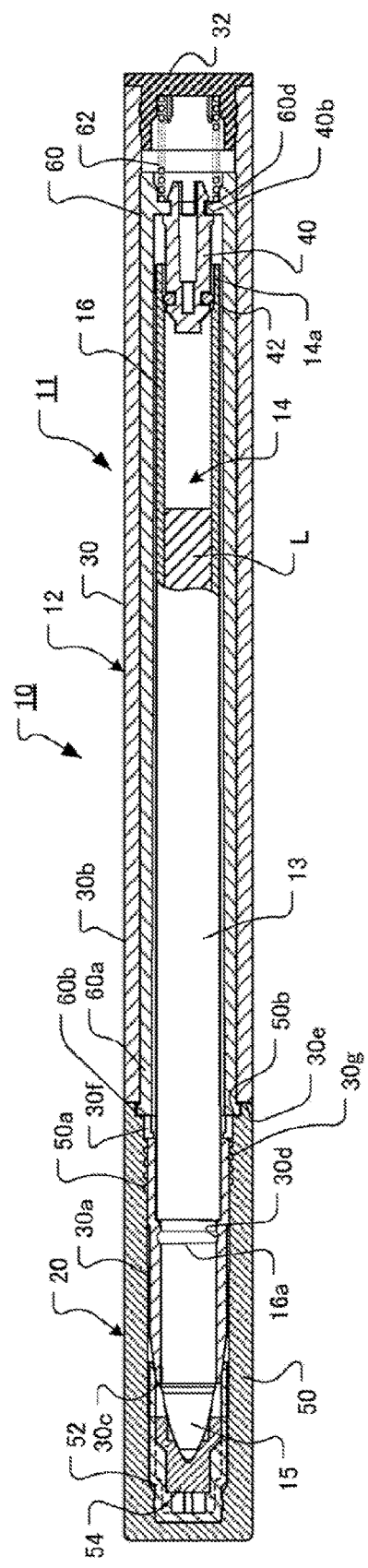
FIG. 1 is an entire sectional view of a liquid applying tool according to a first embodiment of the present invention.

FIGS. 1 to 6(c) show a first embodiment of the present invention. Referring to FIG. 1, a liquid applying tool 10 according to the first embodiment generally includes a liquid storage container 13 having liquid L stored therein, a liquid applicator member 15 provided at a tip end of the liquid storage container 13 for allowing application of the liquid L in the liquid storage container 13 to a target surface, for example, a surface of a sheet of paper, or a surface of the skin of a human user, an outer container 12 externally mounted around the liquid storage container 13 (in other words, the liquid storage container 13 is housed in the outer container 12) in such a manner to allow at least a tip end of the liquid applicator member 15 to be exposed to the outside of the outer container 12, a cap 20 removably mounted to a tip end portion of the outer container 12 to cover the tip end of the liquid applicator member 15, a compression member 40 arranged at a rear end portion of the liquid storage container 13, a forward biasing member 62 for causing the compression member 40 to be biased forward in an axial direction, and a power transmitting member 60 adapted to be reciprocally moved in the axial direction according to attaching/detaching operation of the cap 20. The power transmitting member 60 is disposed between an inner peripheral surface of the outer container 12 and an outer peripheral surface of the liquid storage container 13. Incidentally, a portion of the liquid applying tool 10 except for the cap 20 shall be hereinafter referred to as "a liquid applying tool body 11".

As the liquid to be stored in the liquid storage container 13, there may be employed writing ink, correction liquid, liquid cosmetic, medical liquid, etc. (inclusive of flowable liquid such as gel, and high viscosity liquid).

The respective portions of the liquid applying tool 10 will be discussed in detail hereinafter.

The outer container 12 comprises a tubular shaft 30 opened at tip and rear ends thereof, and a tail plug 32 having a bottomed tubular shape and closing the opened rear end of the tubular shaft 30. The tubular shaft 30 and the tail plug 32 can be formed of synthetic resin, metal, etc. The tail plug 32 is fixed to the rear end portion of the tubular shaft 30 by threading connection, bonding, press-fitting, etc. Incidentally, the outer container 12 may be formed as a one-piece component having a bottomed tubular shape. Although the tubular shaft 30 is formed as a one-piece component in this embodiment, the tubular shaft 30 may be assembled from a plurality of members.

Figure 2:
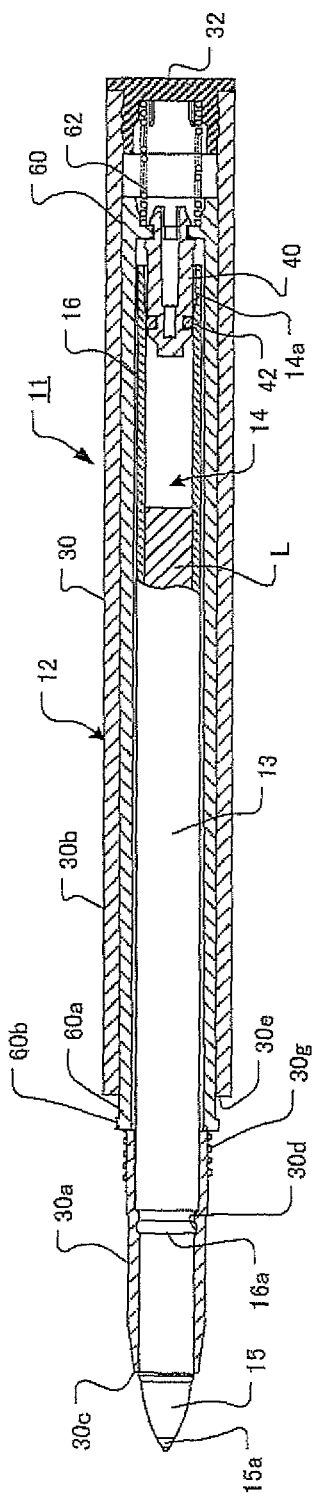
FIG. 2 is an entire sectional view of a body of the liquid applying tool according to the first embodiment.
Figure 3A:
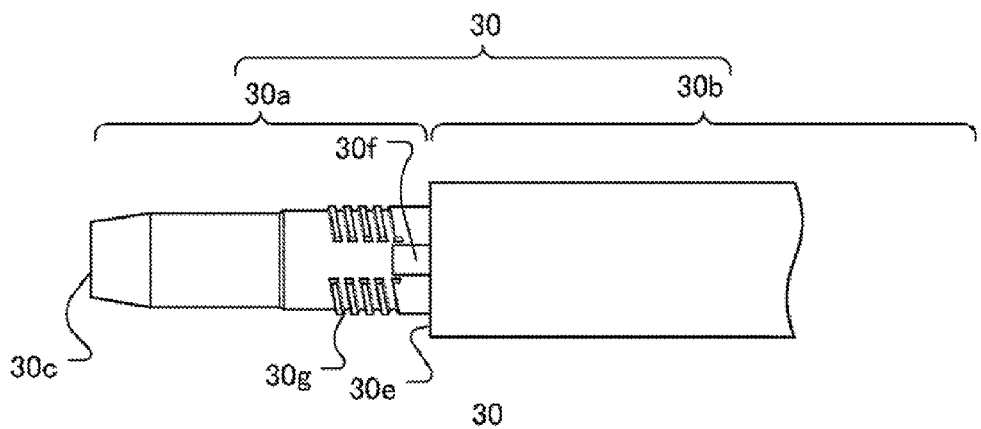
FIG. 3(a) is a fragmentary plane view of a tubular shaft of an outer container of the first embodiment.
Figure 3B:
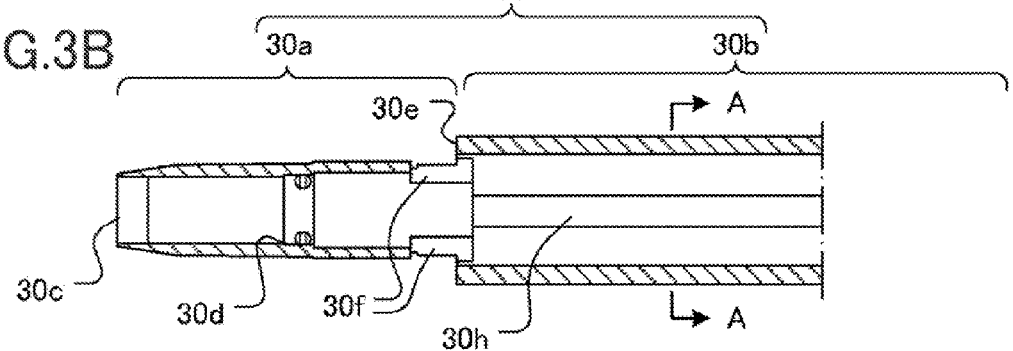
FIG. 3(b) is a fragmentary sectional view of the tubular shaft.
Figure 3C:
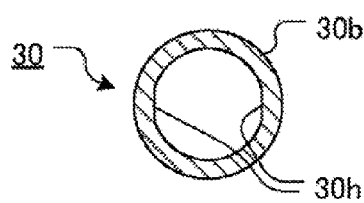
FIG. 3(c) is an A-A sectional view of FIG. 3(b)
Figure 3D:
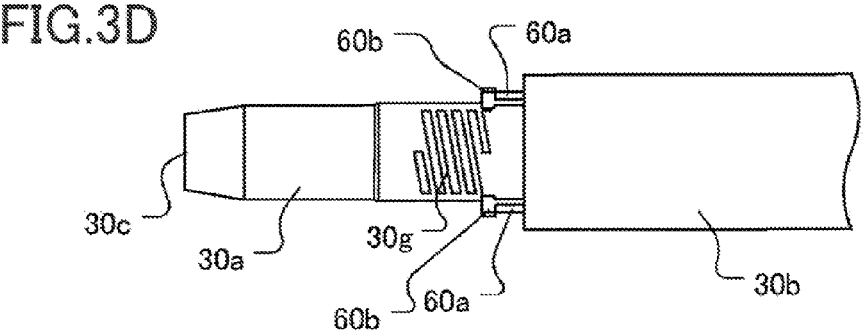
FIG. 3(d) is a fragmentary side view of the tubular shaft in which a power transmitting member is installed.

Referring to FIGS. 2-3(d), the tubular shaft 30 comprises a longitudinal tubular shaft body 30b and a front tubular portion 30a extending forward from a tip end of the tubular shaft body 30b in such a manner that an outer diameter thereof is step-wise reduced. The front tubular portion 30a has a tip end opening 30c formed in a tip end thereof. The tip end 15a of the liquid applicator member 15 of the liquid storage container 13 housed in the outer container 12 is projected out of the outer container 12 through the tip end opening 30c (refer to FIG. 2). Further, the front tubular portion 30a has an annularly recessed engagement portion 30d formed circumferentially around an inner peripheral surface thereof. The tubular shaft 30 is formed with a plurality of axially extending side holes 30f (a pair of axially extending side holes 30f is provided in this embodiment) that extend forward from a boundary step portion 30e between the front tubular portion 30a and the tubular shaft body 30b and are disposed circumferentially around the tubular shaft 30. Moreover, the tubular shaft 30 has an external thread portion 30g formed around an outer peripheral surface of the front tubular portion 30a in the neighborhood of the side holes 30f. As shown in FIG. 3(c), a cross-sectional shape of an inner peripheral surface of the tubular shaft body 30b is not a perfectly circular shape but is of a circular shape with radially inward protruding portions. More particularly, as shown in FIG. 3(b), a plurality of inner peripheral convex portions 30h (in this embodiment, a pair of inner peripheral convex portions 30h) which extend in the axial direction are disposed circumferentially around the inner peripheral surface of the tubular shaft body 30b.

Figure 4:
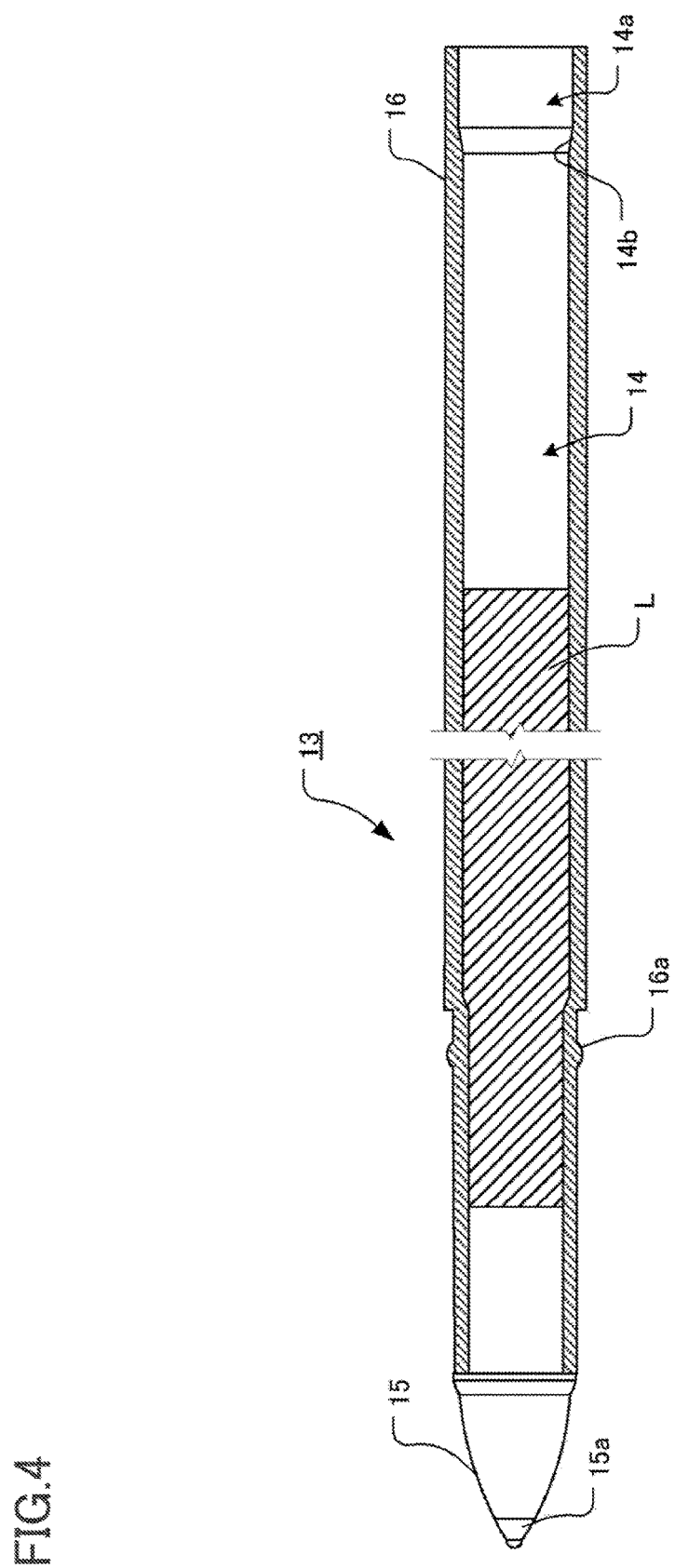
FIG. 4 is a partially sectional plane view of a liquid storage container of the first embodiment.

The liquid storage container 13 which is inserted through the power transmitting member 60 is housed in the outer container 12. Referring to FIG. 4, the liquid storage container 13 comprises a liquid accommodating tube 16 opened at tip and rear ends thereof. The liquid applicator member 15 is fixedly attached to a tip end of the liquid accommodating tube 16. A space that is surrounded by the liquid accommodating tube 16 and the liquid applicator member 15 forms a liquid accommodating chamber 14 having the liquid L stored therein. The liquid accommodating tube 16 has a pressure relief portion 14a which is defined in an interior of the rear end portion of the liquid accommodating tube 16 and whose inner diameter is increased, whereby a sectional area of the pressure relief portion 14a is increased. The pressure relief portion 14a is provided at a tip end portion thereof with a tapered inner surface 14b whose diameter is increased in a rearward direction.

The liquid storage container 13 is inserted in the outer container 12 so as to be axially unmovable with respect to the outer container 12. More particularly, the liquid accommodating tube 16 has an annularly bulged annular-rib 16a provided circumferentially around an outer peripheral surface thereof. As shown in FIG. 2, the annular rib 16a of the liquid accommodating tube 16 is engaged in the recessed engagement portion 30d of the tubular shaft 30 of the outer container 12, whereby the liquid storage container 13 is fixed to the outer container 12 so as to be axially unmovable with respect to the outer container 12.

Although a tip member that holds a ball at a tip end 15a thereof is employed as the liquid applicator member 15 in this embodiment, any suitable tip member that allows the application of liquid, for example, a tip member holding a brush, a felt, a bundle of synthetic fibers, or a porous foam, or a nozzle may be employed as the liquid applicator member 15.

Figure 5A:
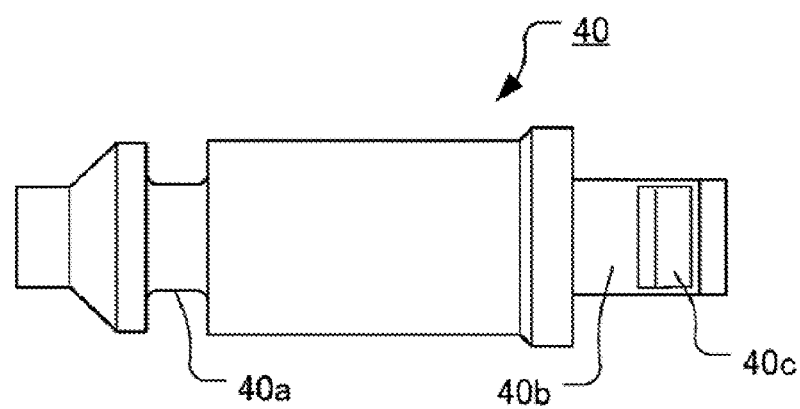
FIG. 5(a) is a plane view of a compression member of the first embodiment.
Figure 5B:
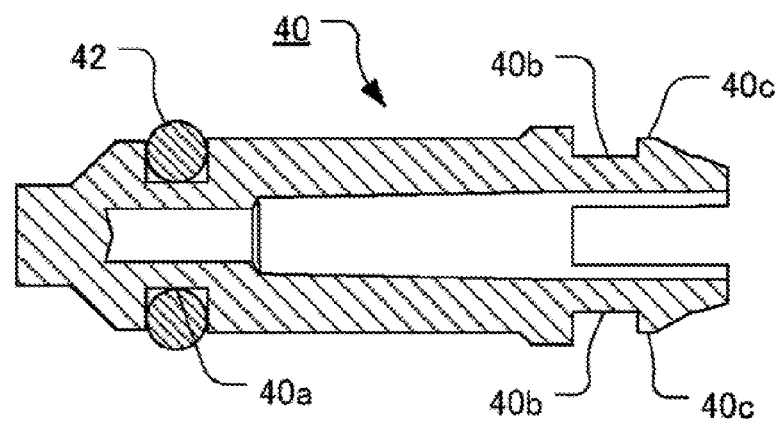
FIG. 5(b) is a sectional view of the compression member.

The compression member 40 is inserted in the pressure relief portion 14*a* from the opened rear end of the liquid accommodating tube 16 so as to be disposed rearward of the liquid L in the liquid accommodating chamber 14, and adapted to be axially reciprocated in the rear end portion of the liquid accommodating tube 16. Referring now to FIGS. 5(*a*) and 5(*b*), the compression member 40 is formed into a substantially tubular shape that is opened at a rear end thereof and closed at a tip end thereof. A tip end portion of the compression member 40 has an annular concave portion 40*a* formed circumferentially around an outer surface thereof. An O-ring-shaped seal member 41 that is formed of elastic material is fitted in the annular concave portion 40*a*. Moreover, a rear end portion of the compression member 40 is provided with a plurality of axially extending elastic pieces 40*b* that are circumferentially spaced apart from one another. Each of the elastic pieces 40*b* has a protrusion 40*c* formed on an outer surface thereof.

When the seal member 42 of the compression member 40 is located in the pressure relief portion 14*a*, a slight clearance allowing air to pass therethrough is adapted to be created between the seal member 42 and the inner peripheral surface of the liquid accommodating tube 16. Incidentally, it is preferable that this clearance is created so as to allow the air to pass therethrough but so as not to allow the liquid L to pass therethrough. When the compression member 40 is moved forward in the liquid accommodating tube 16 and, according to the forward movement of the compression member 40, the seal member 42 reaches a position in front of the tapered inner surface 14*b* of the liquid accommodating tube 16 while being slid on the tapered inner surface 14*b*, the seal member 42 tightly contacts the inner peripheral surface of the liquid accommodating tube 16 to cause the liquid accommodating chamber 14 to be tightly closed, whereby an interior of the liquid accommodating chamber 14 is pressurized. Conversely, when the compression member 40 is moved rearward in the liquid accommodating tube 16 and, according to the rearward movement of the compression member 40, the seal member 42 is moved to the pressure relief portion 14*a* while being slid on the tapered inner surface 14*b*, the clearance is again created between the seal member 42 and the inner peripheral surface of the liquid accommodating tube 16.

As shown in FIG. 1, the cap 20 comprises a tubular cap body 50 opened at an end thereof, an inner cap 52 fixedly disposed in the tubular cap body 50, and a receptacle portion 54 provided in the inner cap 52 so as to be axially movable. The cap body 50 has an inner diameter-increased step portion 50*b* at a rear end portion thereof. Moreover, the cap body 50 has an internal thread portion 50*a* which is provided around an inner peripheral surface of the cap body 50 in front of the inner diameter-increased step portion 50*b* and adapted to be engaged with the external thread portion 30*g* of the tubular shaft 30 which is discussed above. In a state where the cap 20 is removably attached to the tubular shaft 30 with the internal thread portion 50*a* thereof being engaged with the external thread portion 30*g* of the tubular shaft 30, the cap 20 covers the front tubular portion 30*a* of the tubular shaft 30, and the receptacle portion 54 receives the tip end 15*a* of the liquid applicator member 15 to prevent drying of the tip end 15*a* and vaporization of the liquid supplied to the tip end 15*a* of the liquid applicator member 15 from the liquid accommodating chamber 14. Incidentally, in a case where it is unnecessary to prevent the drying of the tip end 15*a* and the vaporization of the liquid, depending upon a kind of the liquid L, the receptacle portion 54 and the inner cap 52 can be omitted.

The power transmitting member 60 is arranged in a radial clearance between the inner peripheral surface of the tubular shaft 30 and the outer peripheral surface of the liquid accommodating tube 16. A spring 62 which serves as a forward biasing member 62 to cause the power transmitting member 60 to be always biased forward is provided between the power transmitting member 60 and the tail plug 32.

Figure 6A:
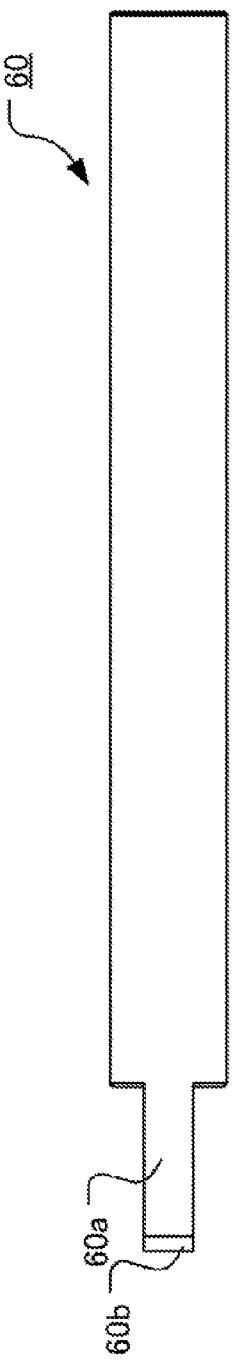
FIG. 6(a) is a plane view of the power transmitting member.
Figure 6B:
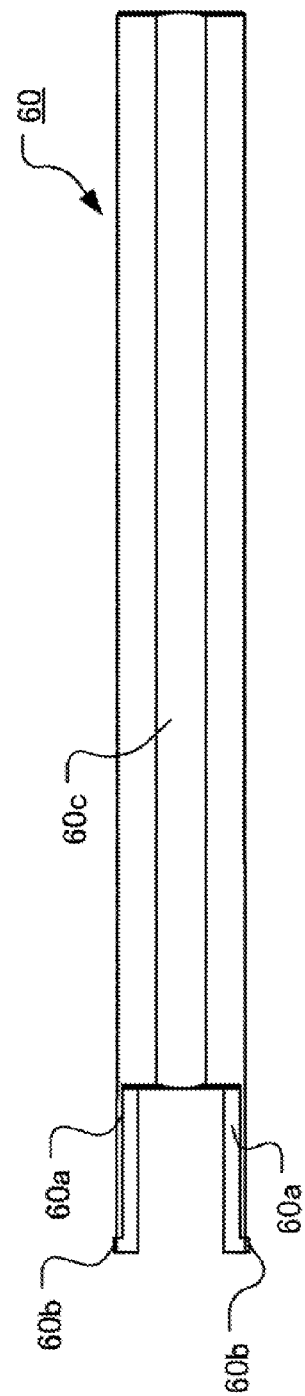
FIG. 6(b) is a side view of the power transmitting member.
Figure 6C:
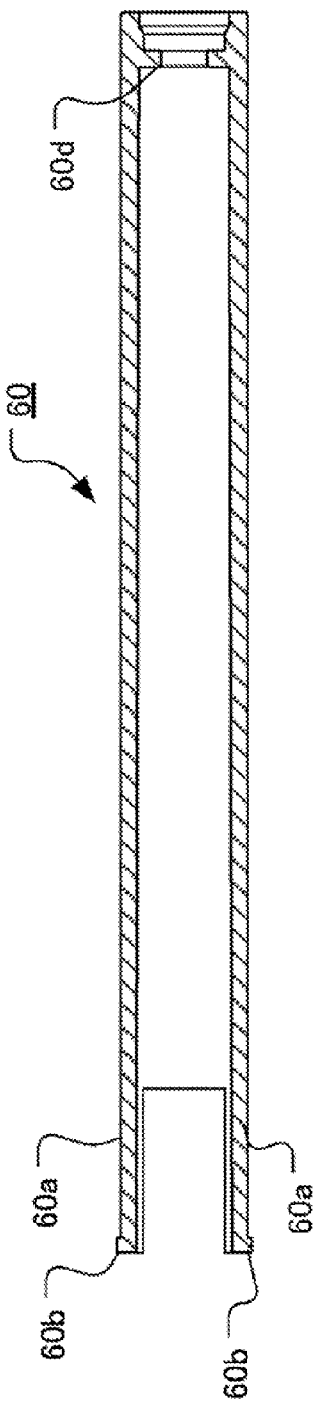
FIG. 6(c) is a vertically sectional view of the power transmitting member.

Referring now to FIGS. 6(*a*)-6(*c*), the power transmitting member 60 comprises a longitudinally extending tubular shaped body, and a plurality of axially extending engagement pieces 60*a* that extend forward from a tip end of the longitudinally extending tubular shaped body (in this embodiment, a pair of axially extending engagement pieces 60*a* is provided). Each of the engagement pieces 60*a* is engaged in corresponding one of the side holes 30*f* of the tubular shaft 30 so as to be exposed to the outside of the side hole 30*f* (refer to FIG. 3(*d*)). A tip end portion of each of the engagement pieces 60*a* is preferably provided with a radially outward protruding portion 60*b*. A cross-sectional shape of an outer peripheral surface of the power transmitting member 60 is not a perfectly circular shape but is of a circular shape with partially cutout portions. More particularly, as shown in FIG. 6(*b*), a plurality of axially extending, outer peripheral concave portions 60*c* are provided circumferentially around the outer peripheral surface of the power transmitting member 60 (in this embodiment, a pair of axially extending, outer peripheral concave portions 60*c* is provided). The outer peripheral concave portions 60*c* are engaged with the inner peripheral convex portions 30*h* of the tubular shaft body 30*b*, whereby the power transmitting member 60 is prevented from rotating with respect to the outer container 12. Moreover, the power transmitting member 60 has a radially inward protruding, annular convex portion 60*d* provided around an inner surface of a rear end portion thereof. The forward biasing member 62 is disposed between a rear end surface of the annular convex portion 60*d* and an inner surface of the tail plug 32. The elastic pieces 40*b* of the compression member 40 are inserted through the annular convex portion 60*d* in such a manner that the annular convex portion 60*d* is allowed to be engaged between a rear end surface of the compression member 40 and the protrusions 40*c* of the elastic pieces 40*b*, whereby the power transmitting member 60 is connected integrally to the compression member 40.

Incidentally, the power transmitting member 60 and the compression member 40 are not always required to be integrally connected. For example, the forward biasing member 62 may be disposed between the tail plug 32 and the compression member 40 in lieu of being disposed between the tail plug 32 and the power transmitting member 60, and the power transmitting member 60 may be adapted to be operatively connected to the compression member 40 in such a manner to allow rearward movement of the power transmitting member 60 to be transmitted to the compression member 40. Moreover, in lieu of being directly connected together, the power transmitting member 60 and the compression member 40 may be adapted to be indirectly connected together. Namely, the power transmitting member 60 shall be acceptable if it is adapted to be operatively connected to one of forward and rearward sides of the compression member 40 in the axial direction.

Although the body of the power transmitting member 60 except for the engagement pieces 60*a* is formed into a longitudinally extending tubular shape in the illustrated embodiment, the shape of the body of the power transmitting member 60 is not always limited to such a shape. For example, any arbitrary shape that extends between the engagement pieces 60a and the compression member 40 may be employed as the shape of the body of the power transmitting member 60.

The operation of the liquid applying tool 10 constructed as discussed above will be explained hereinafter. In the state where the cap 20 is removably attached to the liquid applying tool body 11 as shown in FIG. 1, the external thread portion 30g of the tubular shaft 30 of the outer container 12 and the internal thread portion 50a of the cap body 50 are threadedly engaged with each other, and the rear end edge of the cap 20 is abutted against the boundary step portion 30e between the front tubular portion 30a and the tubular shaft body 30b. Moreover, the inner diameter-increased step portion 50b of the cap body 50 causes the engagement pieces 60a of the power transmitting member 60 to be pushed rearward against the biasing force of the forward biasing member 62. Thus, the power transmitting member 60 and the compression member 40 connected to the power transmitting member 60 are located on the rearward side in the tubular shaft 30, and the seal member 42 of the compression member 40 is located in the pressure relief portion 14a. Therefore, the liquid accommodating chamber 14 is communicated with the outside of the liquid applying tool 10 through a clearance between the seal member 42 and the tapered inner surface 14b of the liquid accommodating tube 16, a clearance between the liquid accommodating tube 16 and the power transmitting member 60, a clearance between the liquid accommodating tube 16 and the tubular shaft 30, and the side holes 30f. In this state, pressure in the liquid accommodating chamber 14 is made equal to atmospheric pressure. Moreover, evaporation of the liquid L in the tip end 15a of the liquid applicator member 15 and drying of the tip end 15a of the liquid applicator member 15 are prevented by the cap 20.

In the above-mentioned state, the cap 20 is first detached from the liquid applying tool body 11 in order that the liquid applying tool 10 is allowed to be used. The detaching operation of the cap 20 from the liquid applying tool body 11 can be performed by causing the cap 20 to be rotated in a predetermined direction with respect to the tubular shaft 30. More particularly, as the cap 20 is rotated in the predetermined direction with respect to the tubular shaft 30, the rear end edge of the cap body 50 is operatively separated from the boundary step portion 30e between the front tubular portion 30a and the tubular shaft body 30b, and the internal thread portion 50a of the cap body 50 and the external thread portion 30g of the tubular shaft 30 are disengaged from each other, whereby the cap 20 is allowed to be removed from the tubular shaft 30 as shown in FIG. 2. Moreover, as the cap 20 is rotated with respect to the tubular shaft 30 in the direction that allows the cap 20 to be detached from the tubular shaft 30, the cap 20 is moved forward with respect to the tubular shaft 30. As the cap 20 is moved forward, the power transmitting member 60 which has been pushed against the inner diameter-increased step portion 50b of the cap body 50 is moved forward in the tubular shaft 30 by the biasing force of the forward biasing member 62, and the compression member 40 connected to the power transmitting member 60 is also moved forward in the liquid accommodating tube 16. As the compression member 40 is moved forward in this way, the seal member 42 is moved forward relative to the tapered inner surface 14b of the liquid accommodating tube 16 and tightly contacted with the inner peripheral surface of the liquid accommodating tube 16 to tightly close the liquid accommodating chamber 14. Thereby, the pressure in the liquid accommodating chamber 14 is pressurized. With the assistance of this pressurizing action, the liquid L in the liquid accommodating chamber 14 can be smoothly fed to the tip end 15a of the liquid applicator member 15. Thus, the liquid fed to the tip end 15a of the liquid applicator member 15 is brought into a state where it is allowed to be applied, via the tip end 15a of the liquid applicator member 15, to the target surface discussed above. According to the liquid applying tool 10 of this embodiment, it is possible to prevent the generation of blurring of the applied liquid and/or the depletion of the liquid in the tip end 15a of the liquid applicator member 15 which will be brought about by insufficient supply of the liquid L to the tip end 15a of the liquid applicator member 15 from the liquid accommodating chamber 14. Moreover, only by the indispensable operation of removing the cap 20 from the outer container 12 which is performed at the time of the use of the liquid applying tool 10, the pressure in the liquid accommodating chamber 14 can be pressurized. Thus, it is possible to generate the pressurizing action without any labor.

After the use of the liquid applying tool 10 is finished, the cap 20 is again attached to the liquid applying tool body 11. First of all, the cap 20 is put on the outer container 12 so as to cover the front tubular portion 30a of the tubular shaft 30 of the outer container 12. In this state, the cap 20 is rotated with respect to the tubular shaft 30 in a direction opposite to the predetermined direction. As the cap 20 is rotated with respect to the tubular shaft 30 in the direction opposite to the predetermined direction, and the internal thread portion 50a of the cap body 50 and the external thread portion 30g of the tubular shaft 30 are operatively engaged with each other, the rear end edge of the cap 20 is abutted against the boundary step portion 30e between the front tubular portion 30a and the tubular shaft body 30b, whereby the cap 20 is perfectly attached to the tubular shaft 30. Moreover, as the cap 20 is rotated with respect to the tubular shaft 30 in the direction that allows the cap 20 to be attached to the tubular shaft 30, the cap 20 is moved rearward with respect to the tubular shaft 30. As the cap 20 is moved rearward, the inner diameter-increased step portion 50b of the cap body 50 causes the engagement pieces 60a of the power transmitting member 60 to be pushed rearward, whereby the power transmitting member 60 is moved rearward in the tubular shaft 30 against the biasing force of the forward biasing member 62. By the rearward movement of the power transmitting member 60, the compression member 40 is also moved rearward. As the compression member 40 is moved rearward, the seal member 42 is located in the pressure relief portion 14a, the clearance between the seal member 42 and the inner peripheral surface of the liquid accommodating tube 16 is again created, and the pressure in the liquid accommodating chamber 14 is returned to the pressure equal to the atmospheric pressure (refer to FIG. 1).

Thus, every time the cap 20 is removed from the outer container 12, the liquid accommodating chamber 14 is pressurized, and every time the cap 20 is attached to the outer container 12, the liquid accommodating chamber 14 is released from the pressurized state. Incidentally, in this embodiment, in order to allow the cap 20 to be removably attached to the outer container 12, the external thread portion 30g is formed on the outer peripheral surface of the outer container 12, the internal thread portion 50a is formed on the inner peripheral surface of the cap 20, and the external thread portion 30g and the internal thread portion 50a are threadedly engaged with each other. However, the present invention is not limited to such a case and the cap 20 may be removably attached to the outer container 12 by using any suitable conventional coupling means. For example, an outer convex portion may be formed around the outer peripheral surface of the outer container 12, an inner convex portion may be formed around the inner peripheral surface of the cap 20, the outer convex portion of the outer container 12 and the inner convex portion of the cap 20 may be engaged with each other. Moreover, the inner peripheral surface of the opened side of the cap 20 may be configured to be engaged with the outer peripheral surface of the outer container 12.

(Second Embodiment)

Next, a liquid applying tool according to a second embodiment of the present invention will be discussed hereinafter. In the first embodiment discussed above, according to the attaching/detaching operation of the cap 20 with respect to the outer container 12, the power transmitting member 60 is adapted to be axially reciprocated in the outer container 12 and the compression member is adapted to be axially reciprocated with respect to the liquid storage container 13. On the other hand, in the second embodiment, according to the attaching/detaching operation of a cap 120 with respect to an outer container 112, a power transmitting member 160 is adapted to be axially reciprocated in the outer container 112, and a liquid storage container 113 is adapted to be axially reciprocated relative to a compression member 140.

FIGS. 7-11(b) illustrate the second embodiment. Reference numeral 110 that is employed in any of these figures denotes a liquid applying tool according to the second embodiment. The liquid applying tool 110 generally includes a liquid storage container 113 having liquid L stored therein, a liquid applicator member 115 provided at a tip end of the liquid storage container 113, an outer container 112 externally mounted around the liquid storage container 113 (in other words, the liquid storage container 113 is housed in the outer container 112) in such a manner to allow at least a tip end of the liquid applicator member 115 to be exposed to the outside of the outer container 112, a cap 120 removably mounted to a tip end portion of the outer container 112 to cover the tip end of the liquid applicator member 115, a compression member 140 arranged at a rear end portion of the liquid storage container 113, a rearward biasing member 162 biasing the liquid storage container 113 rearward in an axial direction, and a power transmitting member 160 adapted to be reciprocated in the axial direction according to attaching/detaching operation of the cap 20 with respect to the outer container 112. The power transmitting member 160 is disposed between an inner peripheral surface of the outer container 112 and an outer peripheral surface of the liquid storage container 113. The respective portions of the second embodiment will be discussed in detail hereinafter by focusing on differences of the respective portions from those of the first embodiment.

The outer container 112 comprises a tubular shaft 130 opened at tip and rear ends thereof, and a tail plug 132 having a bottomed tubular shape and closing the opened rear end of the tubular shaft 130. Incidentally, the tail plug 132 has an annularly bulged annular-rib 132a formed circumferentially around an inner peripheral surface thereof (refer to FIG. 10(b)).

Figure 8:
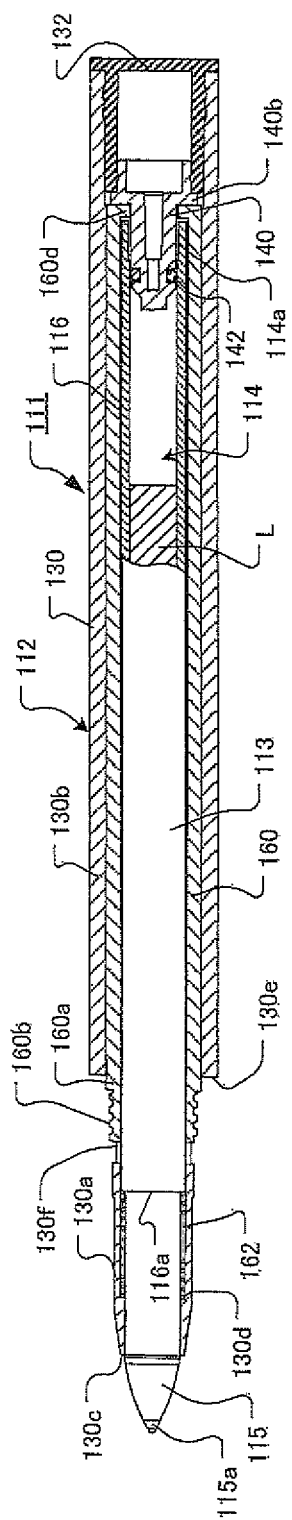
FIG. 8 is an entire sectional view of a body of the liquid applying tool according to the second embodiment.
Figure 9A:
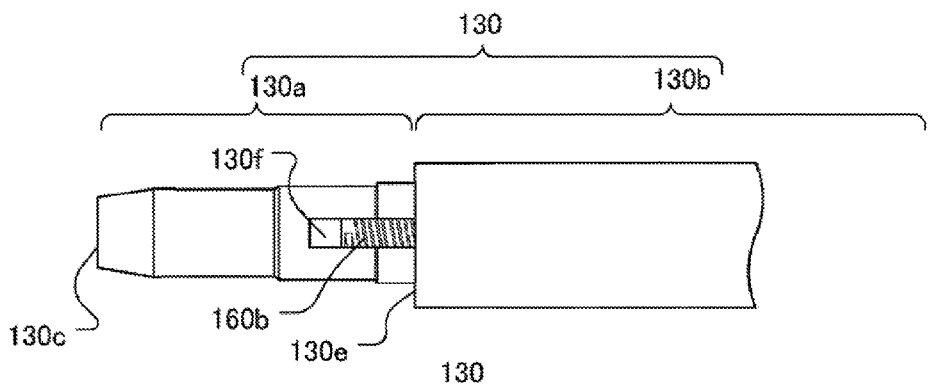
FIG. 9(a) is a fragmentary plane view of a tubular shaft of an outer container of the second embodiment in which a power transmitting member of the second embodiment is installed.
Figure 9B:
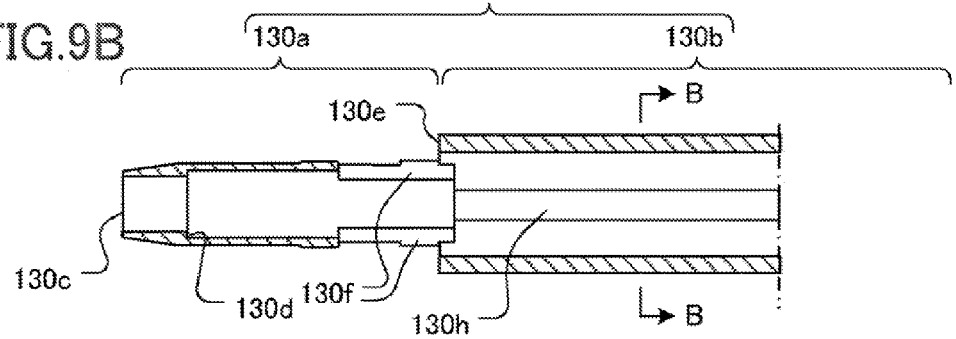
FIG. 9(b) is a fragmentary sectional view of the tubular shaft of the second embodiment.
Figure 9C:
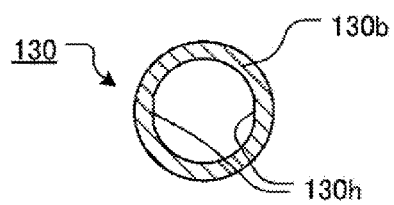
FIG. 9(c) is a B-B sectional view of FIG. 9(b)
Figure 9D:
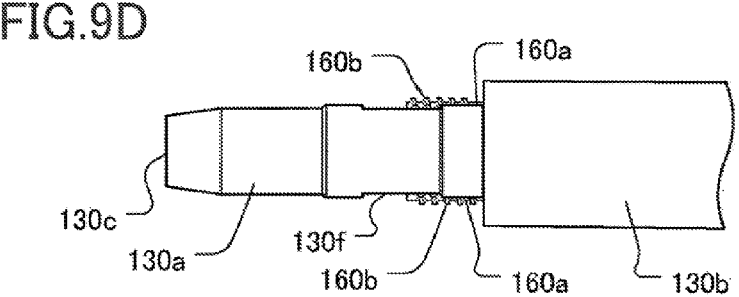
FIG. 9(d) is a fragmentary side view of the tubular shaft to which the power transmitting member is installed.

Referring to FIGS. 8-9(d), the tubular shaft 130 comprises a longitudinal tubular shaft body 130b, and a front tubular portion 130a which extends forward from a tip end of the tubular shaft body 130b and whose outer diameter is stepwise reduced from the tip end of the tubular shaft body 130b.

The front tubular portion 130a has a tip end opening 130c from which the tip end 115a of the liquid applicator member 115 is projected outward (refer to FIG. 8). Moreover, the tubular shaft 130 has a plurality of axially extending side holes 130f (in this embodiment, a pair of axially extending side holes 130f is provided) formed circumferentially around a peripheral surface thereof. The plurality of axially extending side holes 130f extend forward from a boundary step portion 130e between the front tubular portion 130a and the tubular shaft body 130b and are similar to the side holes 30f of the tubular shaft 30 of the first embodiment. As shown in FIG. 9(c), a cross-sectional shape of an inner peripheral surface of the tubular shaft body 130b is not a perfectly circular shape but is of a circular shape with radially inward protruding portions. More particularly, as shown in FIG. 9(b), the tubular shaft body 130b has a plurality of axially extending, inner peripheral convex portions 130h (in this embodiment, a pair of axially extending, inner convex portions 130h are provided) disposed circumferentially around the inner peripheral surface thereof. Moreover, a step portion 130d is provided around an inner peripheral surface of the front tubular portion 130a.

The liquid storage container 113 which is inserted through the power transmitting member 160 is housed in the outer container 112. The liquid storage container 113 comprises a liquid accommodating tube 116 opened at tip and rear ends thereof. The liquid applicator member 115 for allowing application of the liquid L in the liquid accommodating tube 116 to a target surface, for example, a surface of a sheet of paper, or a surface of the skin of a human user is fixedly mounted to a tip end of the liquid accommodating tube 116. A space that is surrounded by the liquid accommodating tube 116 and the liquid applicator member 115 forms a liquid accommodating chamber 114 having the liquid L stored therein. Like the liquid accommodating tube 16 of the first embodiment, the liquid accommodating tube 116 of the second embodiment has a pressure relief portion 114a which is defined in an interior of the rear end portion of the liquid accommodating tube 116 and whose inner diameter is increased, whereby a sectional area of the pressure relief portion 114a is increased. The pressure relief portion 114a is provided at a tip end portion thereof with a tapered surface (not shown; similar to the tapered inner surface 14b of the pressure relief portion 14a of the first embodiment) whose inner diameter is increased toward a rearward direction. Moreover, the liquid accommodating tube 116 has a step portion 116a provided around the outer peripheral surface of the tip end portion thereof.

Moreover, in the second embodiment, a spring 162 serving as a rearward biasing member for causing the liquid storage container 113 to be always biased rearward is mounted around the outer peripheral surface of the tip end portion of the liquid storage container 113. The rearward biasing member 162 is disposed between the step portion 130d of the front tubular portion 130a of the tubular shaft 130 and the step portion 116a of the liquid accommodating tube 116.

Figure 10A:
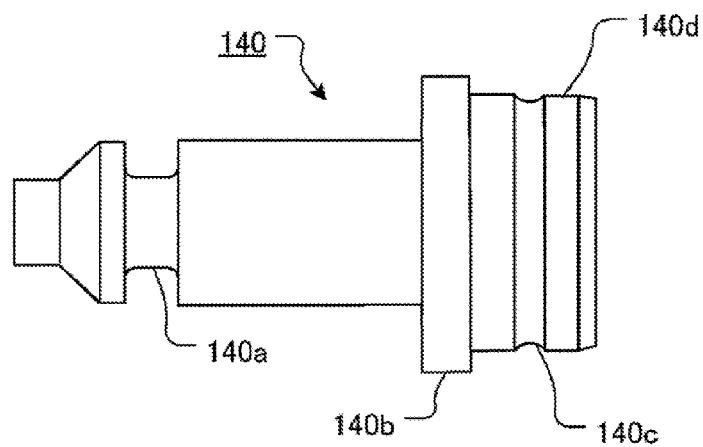
FIG. 10(a) is a plane view of a compression member of the second embodiment.
Figure 10B:
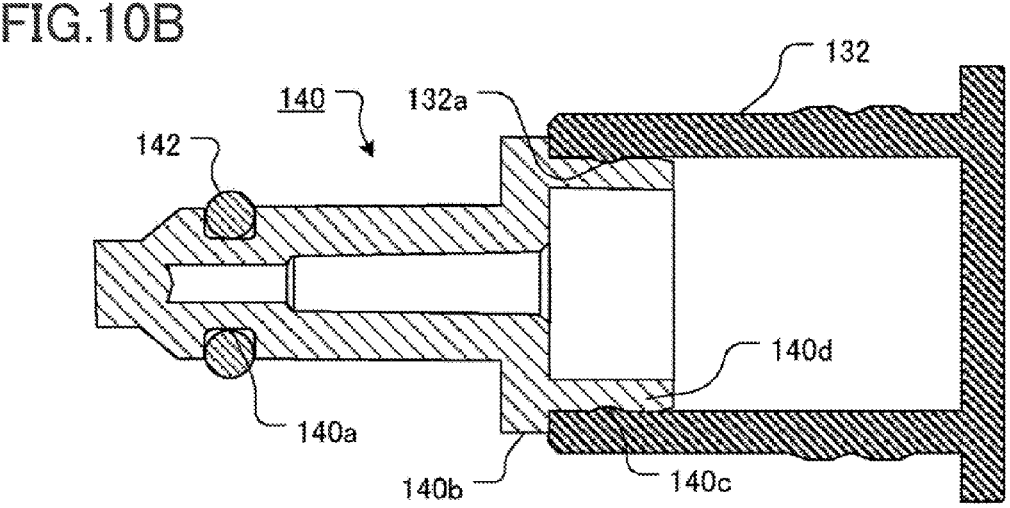
FIG. 10(b) is a sectional view of the power transmitting member and tail plug of the second embodiment.

Referring to FIGS. 10(a) and 10(b), the compression member 140 is formed in a substantially tubular shape and has an opened rear end portion and a closed tip end portion. The tip end portion of the compression member 140 has an annular concave portion 140a formed around the outer peripheral surface thereof. An O-ring-shaped seal member 142 which is formed of elastic material is fitted in the annular concave portion 140a. Moreover, a flange portion 140b is formed around the outer peripheral surface of the rear end portion of the compression member 140. A region of the rear end portion of the compression member 140 in the rear of the flange portion 140b is formed with an engagement portion 140d which is engaged in the tail plug 132. More particularly, the engagement portion 140d has an engaging concave portion 140c which is annularly formed circumferentially around the outer peripheral surface of the engagement portion 140d. The engagement portion 140d of the compression member 140 is fitted in the tail plug 132 in such a manner that the engaging concave portion 140c thereof is engaged with the annular rib 132a of the tail plug 132, whereby the compression member 140 is fixedly connected to the tail plug 132. Moreover, the compression member 140 is inserted in the pressure relief portion 114a from the rear end opening of the liquid accommodating tube 116 and located rearward of the liquid L in the liquid accommodating chamber 114.

When the seal member 142 of the compression member 140 is located in the pressure relief portion 114a, a slight clearance for allowing the passage of air only is adapted to be created between the seal member 142 and the inner peripheral surface of the liquid accommodating tube 116. Incidentally, it is preferable that this clearance is configured so as to allow the passage of air but so as not to allow the passage of the liquid. When the power transmitting member 160 and the liquid storage container 113 are moved rearward in the tubular shaft 130, the compression member 140 is moved forward relative to the liquid accommodating tube 116. As the compression member 140 is moved forward, the seal member 142 is slid on the tapered surface of the liquid accommodating tube 116 and reaches a position in the front of the tapered surface of the liquid accommodating tube 116. Thereby, the seal member 142 tightly contacts the inner peripheral surface of the liquid accommodating tube 116 to tightly close the liquid accommodating chamber 114, and the liquid accommodating chamber 114 is pressurized. On the other hand, when the power transmitting member 160 and the liquid storage container 113 are moved forward in the tubular shaft 130, the compression member 140 is moved rearward relative to the liquid accommodating tube 116. As the compression member 140 is moved rearward relative to the liquid accommodating tube 116, the seal member 142 is slid on the tapered surface of the liquid accommodating tube 116 and moved to the pressure relief portion 114a. Thereby, the clearance is again created between the seal member 142 and the inner peripheral surface of the liquid accommodating tube 116.

The power transmitting member 160 is disposed in a radial clearance between the inner peripheral surface of the tubular shaft 130 and the outer peripheral surface of the liquid accommodating tube 116.

Figure 7:
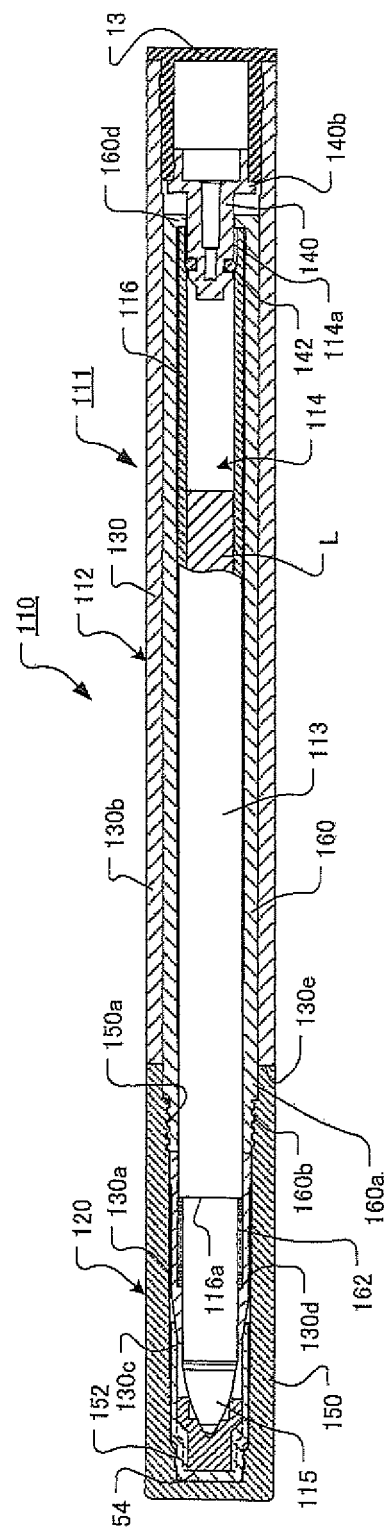
FIG. 7 is an entire sectional view of a liquid applying tool according to a second embodiment of the present invention.

Referring to FIGS. 11(a) and 11(b), the power transmitting member 160 comprises a longitudinal tubular-shaped body and a plurality of axially extending engagement pieces 160a (in this embodiment, a pair of engagement pieces 160a are provided) which extend forward from the tip end of the longitudinal tubular-shaped body of the power transmitting member 160. Each of the engagement pieces 160a is engaged in corresponding one of the side holes 130f of the tubular shaft 130 so as to be exposed to the outside of the tubular shaft 130 from the side hole 130f. Moreover, an outer surface of the engagement piece 160a which is exposed from the side hole 130f is provided with an external thread portion 160b. A cross-sectional shape of the outer peripheral surface of the body of the power transmitting member 160 is not a perfectly circular shape and is of a circular shape with partially cutout portions. As shown in FIG. 11(b), a plurality of axially extending, outer peripheral concave portions 160c (in this embodiment, a pair of axially extending, outer concave portions 160c are provided) are disposed circumferentially around the outer peripheral surface of the body of the power transmitting member 160. By engagement between the outer peripheral concave portions 160c of the power transmitting member 160 and the inner peripheral convex portions 130h of the tubular shaft body 130b, the power transmitting member 160 is prevented from rotating with respect to the outer container 112. Moreover, the power transmitting member 160 and the compression member 140 are operatively connected to each other. More particularly, as shown in FIGS. 7 and 8, the power transmitting member 160 has an annular convex portion 160d which protrudes radially inward from the rear end of the power transmitting member 160. The compression member 140 is inserted through the annular convex portion 160d so as to be movable relative to the power transmitting member 160. Moreover, a front surface of the annular convex portion 160d of the power transmitting member 160 is abutted on a rear end edge of the liquid accommodating tube 116, whereby forward movement of the power transmitting member 160 is transmitted to the liquid storage container 113. Incidentally, the power transmitting member 160 and the liquid storage container 113 may be integrally connected to each other. Moreover, although the body of the power transmitting member 160 is formed into a tubular shape in the illustrated example, the shape of the body of the power transmitting member 160 is not always limited to such a shape. It may be formed into an arbitrary shape that extends between the engagement pieces 160a and the liquid accommodating tube 116.

As discussed above, the spring 162 which serves as the rearward biasing member to cause the liquid storage container 113 to be always biased rearward is provided around the outer peripheral surface of the tip end portion of the liquid accommodating tube 116. The rearward biasing member 162 is disposed between the step portion 130d of the front tubular portion 130a of the tubular shaft 130 and the step portion 116a of the liquid accommodating tube 116. The liquid accommodating tube 116 which is biased rearward by the rearward biasing member 162 pushes the annular convex portion 160d of the power transmitting member 160 with the rear end portion thereof and is adapted to be movable rearward until the rear end of the power transmitting member 160 is abutted against the flange portion 140b of the compression member 140.

The cap 120 comprises a tubular cap body 150 opened at one end thereof, an inner cap 152 fixed in the cap body 150, and a receptacle portion 154 disposed in the inner cap 152 so as to be movable in a forward/rearward direction. The cap body 150 has an internal thread portion 150a which is threadedly engaged with the external thread portions 160b of the power transmitting member 160 and formed around the inner peripheral surface of a region of the cap body 150 which is adjacent to the opened end of the cap body 150. In the state where the internal thread portion 150a and the external thread portions 160b are threadedly engaged with each other, the front tubular portion 130a of the tubular shaft 130 is covered with the cap 120 and the receptacle portion 154 receives and covers the tip end 115a of the liquid applicator member 115 to thereby prevent vaporization of the liquid L in the tip end 115a of the liquid applicator member 115 and drying of the tip end 115a of the liquid applicator member 115. Incidentally, in a case where the vaporization of the liquid in the tip end 115a of the liquid applicator member 115 and drying of the tip end 115a of the liquid applicator member 115 are not required to be considered depending upon the kind of the liquid, the receptacle portion 154 and the inner cap 152 may be omitted.

The operation of the liquid applying tool 110 constructed as discussed above will be discussed hereinafter. In the state where the cap 120 is attached to the liquid applying tool body 111 as shown in FIG. 7, the external thread portions 160b of the engagement pieces 160a of the power transmitting member 160 and the internal thread portion 150a of the cap body 150 are threadedly engaged with each other, and the rear end edge of the cap 120 is abutted against the boundary step portion 130e between the front tubular portion 130a and the tubular shaft body 130b of the tubular shaft 130. Moreover, by the threaded engagement between the internal thread portion 150a of the cap body 150 and the external thread portions 160b of the engagement pieces 160a of the power transmitting member 160, the cap 120 causes the engagement pieces 160a of the power transmitting member 160 to be pulled forward against the biasing force of the rearward biasing member 162. In this state, the power transmitting member 160 and the liquid storage container 113 forward pushed against the annular convex portion 160d of the power transmitting member 160 are located at a front position in the tubular shaft 130, and the seal member 142 of the compression member 140 is located in the pressure relief portion 114a. Therefore, the liquid accommodating chamber 114 is communicated with the outside of the liquid applying tool 110 through the clearance between the seal member 142 and the tapered surface of the liquid accommodating tube 116, the clearance between the liquid accommodating tube 116 and the power transmitting member 160, the clearance between the liquid accommodating tube 116 and the tubular shaft 130, and the side holes 130f of the tubular shaft 130. Thus, pressure in the liquid accommodating chamber 114 becomes equal to the atmospheric pressure. Moreover, the vaporization of the liquid in the tip end 115a of the liquid applicator member 115 and drying of the tip end 115a of the liquid applicator member 115 are prevented by the cap 120.

When the liquid applying tool 110 is used, first of all, the cap 120 is removed from the liquid applying tool body 111. In this case, the cap 120 is rotated with respect to the tubular shaft 130 in a predetermined direction. As the cap 120 is rotated in this way, the rear end edge of the cap body 150 is separated from the boundary step portion 130e of the tubular shaft 130, and the internal thread portion 150a of the cap body 150 is disengaged from the external thread portions 160b of the engagement pieces 160a of the power transmitting member 160. Thus, the cap 120 can be removed from the tubular shaft 130 as shown in FIG. 8. Moreover, as the internal thread portion 150a of the cap body 150 is disengaged from the external thread portions 160b of the engagement pieces 160a of the power transmitting member 160 in this way by causing the cap 120 to be rotated in the predetermined direction, the liquid storage container 113 which has been forcedly located in the front position by the power transmitting member 160 is moved rearward by the biasing force of the rearward biasing member 162. Therefore, the annular convex portion 160d of the power transmitting member 160 is pushed by the rear end edge of the liquid storage container 113, whereby the power transmitting member 160 is moved rearward in the tubular shaft 130. By the rearward movement of the liquid storage container 113, the compression member 140 is moved forward relative to the liquid accommodating tube 116, and the seal member 142 is slid on the tapered surface of the liquid accommodating tube 116 and then reaches a position in the front of the tapered surface. When the seal member 142 reaches the position, it tightly contacts the inner peripheral surface of the liquid accommodating tube 116, whereby the liquid accommodating chamber 114 is tightly closed and then pressurized. With the assistance of this pressurizing action, the liquid L in the liquid accommodating chamber 114 can be smoothly supplied to the tip end 115a of the liquid applicator member 115 and the tip end 115a of the liquid applicator member 115 is brought to a state where it can apply the liquid to a target surface, for example, a surface of a sheet of paper, and a surface of the skin of a human user. According to the liquid applying tool 110 of this embodiment, it is possible to prevent the generation of blurring of the applied liquid and/or the depletion of the liquid in the tip end 115a of the liquid applicator member 115 which will be brought about by insufficient supply of the liquid L to the tip end 115a of the liquid applicator member 115 from the liquid accommodating chamber 114. Moreover, only by the indispensable operation of removing the cap 120 from the outer container 112 which is performed at the time of the use of the liquid applying tool 110, the pressure in the liquid accommodating chamber 14 can be pressurized. Thus, it is possible to create the pressurizing action without any labor.

After the use of the liquid applying tool 110 is finished, the cap 120 is again attached to the liquid applying tool body 111. In this case, first of all, the cap 120 is put on the outer container 112 so as to cover the front tubular portion 130a of the tubular shaft 130. In this state, when the cap 120 is rotated with respect to the tubular shaft 130 in a direction opposite to the predetermined direction, the external thread portions 160b of the engagement pieces 160a of the power transmitting member 160 and the internal thread portion 150a of the cap body 150 are operatively engaged with each other. As the internal thread portion 150a of the cap body 150 and the external thread portions 160b of the engagement pieces 160a of the power transmitting member 160 are operatively engaged with each other in this way, the rear end edge of the cap 120 is abutted against the boundary step portion 130e between the front tubular portion 130a and the tubular shaft body 130b of the tubular shaft 130. Thus, the cap 120 is perfectly attached to the tubular shaft 130. Moreover, as the internal thread portion 150a of the cap body 150 and the external thread portions 160b of the engagement pieces 160a of the power transmitting member 160 are operatively engaged with each other, the cap 120 causes the engagement pieces 160a of the power transmitting member 160 to be pulled forward against the biasing force of the rearward biasing member 162, whereby the power transmitting member 160 is moved forward in the tubular shaft 130. As the power transmitting member 160 is moved forward, the annular convex portion 160d of the power transmitting member 160 pushes the rear end edge of the liquid accommodating tube 116 to thereby move the liquid storage container 113 forward in the tubular shaft 130. By the forward movement of the liquid storage container 113, the compression member 140 is moved rearward relative to the liquid accommodating tube 116, whereby the seal member 142 is returned to the pressure relief portion 114a and the clearance is again created between the seal member 142 and the inner peripheral surface of the liquid accommodating tube 116, and the pressure in the liquid accommodating chamber 114 is returned to the pressure equal to the atmospheric pressure (refer to FIG. 7).

Thus, every time the attaching/detaching operation of the cap 120 is performed, releasing of the liquid accommodating chamber 114 from the pressurized state and pressurizing of the liquid accommodating chamber 114 can be repeated. Incidentally, in the first and second embodiments, the power transmitting members 60, 160 are prevented from being rotated relative to the outer containers 12, 112 by the engagement between the inner peripheral convex portions 30h, 130h, which are formed on the inner peripheral surfaces of the tubular shafts 30, 130, and the outer peripheral concave portions 60c, 160c which are formed on the outer peripheral surfaces of the power transmitting members 60, 160. However, the mechanisms for preventing the power transmitting members 60, 160 from being rotated relative to the outer containers 12, 112 are not limited to such mechanisms and any suitable conventional mechanisms for preventing the power transmitting members 60, 160 from being rotated relative to the outer containers 12, 112 can be employed. For example, as the rotation preventing mechanisms, there may be employed rotation preventing mechanisms which comprise axially extending groove portions formed in the inner peripheral surfaces of the tubular shaft bodies 30b, 130b of the tubular shafts 30, 130, and convex portions formed on the outer peripheral surfaces of the power transmitting members 60, 160 and adapted to be engaged in the axially extending groove portions. Moreover, for example, the cross-sectional shapes of the inner peripheral surfaces of the tubular shafts 30, 130 are formed into polygonal shapes, elliptical shapes, etc., and the cross-sectional shapes of the outer peripheral surfaces of the power transmitting members 60, 160 are formed into polygonal shapes, elliptical shapes, etc., whereby the power transmitting members 60, 160 can be prevented from being rotated with respect to the outer containers 12, 112.

(Third Embodiment)

Figure 12:
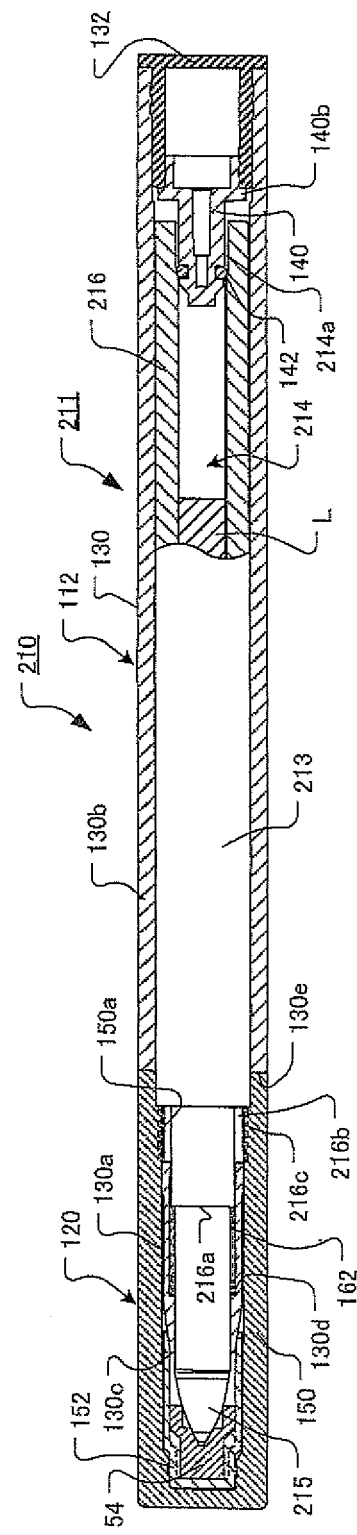
FIG. 12 is an entire sectional view of a liquid applying tool according to a third embodiment of the present invention.
Figure 13:
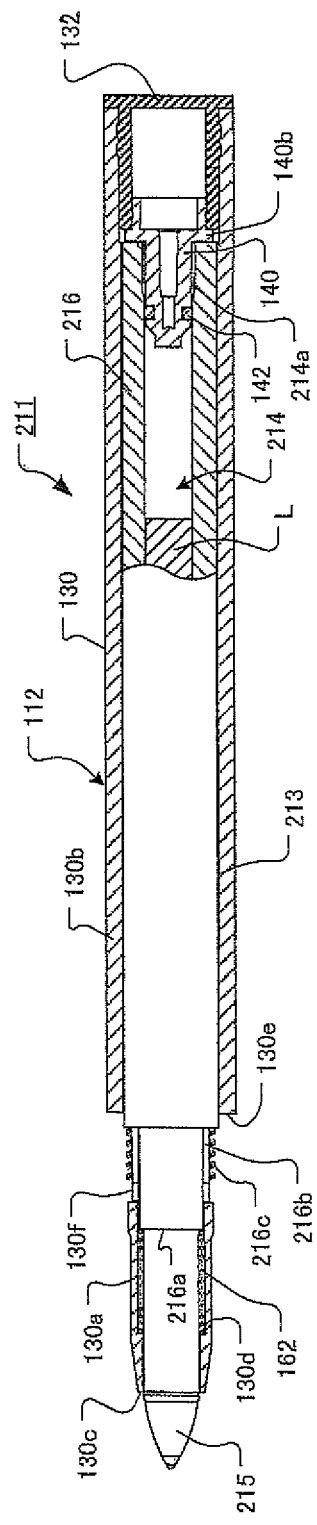
FIG. 13 is an entire sectional view of a body of the liquid applying tool according to the third embodiment of the present invention.

Next, a liquid applying tool 210 according to a third embodiment of the present invention will be discussed hereinafter with reference to FIGS. 12 and 13. The third embodiment is a modification of the second embodiment. Therefore, components of the third embodiment which are identical or similar to those of the second embodiment are denoted with like reference signs and detailed description of them is omitted.

In the second embodiment, the liquid accommodating tube 116 and the power transmitting member 160 are formed as separate components, namely, the liquid storage container 113 and the power transmitting member 160 are formed as separate components. The third embodiment is different from the second embodiment in that the third embodiment includes a liquid accommodating tube 216 formed integrally with a power transmitting member, namely, a liquid storage container 213 formed integrally with the power transmitting member. Incidentally, since a liquid accommodating chamber 214, a pressure relief portion 214a, a liquid applicator member 215, and a step portion 216a of the third embodiment are similar to the liquid accommodating chamber 114, the pressure relief portion 114a, the liquid applicator member 115, and the step portion 116 of the second embodiment, respectively, detailed description of them is omitted.

Like the rear end portions of the liquid accommodating tubes 16, 116 of the first and second embodiments, the rear end portion of the liquid accommodating tube 216 of the third embodiment is increased in an inner diameter thereof to thereby form the pressure relief portion 214a which has an increased sectional area. A tip end portion of the pressure relief portion 214a has a tapered inner surface (not shown; similar to the tapered inner surface 14b of the first embodiment) whose diameter is increased toward a rearward direction. Moreover, the outer peripheral surface of the tip end portion of the liquid accommodating tube 216 has a step portion 216a whose diameter is step-wise increased toward the rearward direction.

The spring which serves as the rearward biasing member 162 for causing the liquid storage container 213 to be always biased rearward is mounted around the outer peripheral surface of the tip end portion of the liquid storage container 213. The rearward biasing member 162 is disposed between the step portion 130d of the front tubular portion 130a of the tubular shaft 130 and the step portion 216a of the liquid accommodating tube 216.

Radially outward protruding engagement protrusions 216b are provided on portions of an outer periphery of the liquid accommodating tube 216 which positionally correspond to the side holes 130f of the front tubular portion 130a of the tubular shaft 130. The engagement protrusions 216b are engaged in the side holes 130f. The engagement protrusions 216b are formed with external thread portions 216c which are engaged with the internal thread portion 150a of the cap body 150 of the cap 120.

The operation of the liquid applying tool 210 constructed as discussed above will be explained hereinafter. In a state where the cap 120 is attached to a liquid applying tool body 211 as shown in FIG. 12, the external thread portions 216c of the engagement protrusions 216b of the liquid accommodating tube 216 and the internal thread portion 150a of the cap body 150 of the cap 120 are threadedly engaged with one another, and the rear end edge of the cap 120 is abutted against the boundary step portion 130e between the front tubular portion 130a and tubular shaft body 130b of the tubular shaft 130. Moreover, the internal thread portion 150a of the cap body 150 is threadedly engaged with the external thread portions 216c of the liquid accommodating tube 216, whereby the cap 120 causes the liquid accommodating tube 216 to be pulled forward against the biasing force of the rearward biasing member 162. Thus, the liquid storage container 213 is located at a forward position in the tubular shaft 130 and the seal member 142 of the compression member 140 is located in the pressure relief portion 214a. Therefore, the liquid accommodating chamber 214 is communicated with the outside of the liquid applying tool 210 through the clearance between the seal member 142 and the tapered surface of the liquid accommodating tube 216, the clearance between the liquid accommodating tube 216 and the tubular shaft 130, and the side holes 130f, so that the pressure in the liquid accommodating chamber 214 is made equal to the atmospheric pressure.

When the liquid applying tool 210 in the above-mentioned state is used, the cap 120 is removed from the liquid applying tool body 211. The removal of the cap 120 from the liquid applying tool body 211 is performed by causing the cap 120 to be rotated in a predetermined direction with respect to the tubular shaft 130. More particularly, as the cap 120 is rotated in the predetermined direction with respect to the tubular shaft 130, the rear end edge of the cap body 150 is separated from the boundary step portion 130e between the front tubular portion 130a and tubular shaft body 130b of the tubular shaft 130, and the internal thread portion 150a of the cap body 150 is disengaged from the external thread portions 216c of the engagement protrusions 216b, whereby the cap 120 is removed from the tubular shaft 130 as shown in FIG. 13. Moreover, as the internal thread portion 150a of the cap body 150 is disengaged from the external thread portions 216c of the engagement protrusions 216b in this way by causing the cap 120 to be rotated in the predetermined direction with respect to the tubular shaft 130, the liquid storage container 213 which has been located at the forward position is moved rearward by the biasing force of the rearward biasing member 162. By the rearward movement of the liquid storage container 213, the compression member 140 is moved forward relative to the liquid accommodating tube 216. As the compression member 140 is moved forward, the seal member 142 reaches a position in front of the tapered surface of the liquid accommodating tube 216 and tightly contacts the inner peripheral surface of the liquid accommodating chamber 214, whereby the liquid accommodating chamber 214 is tightly closed and an interior of the liquid accommodating chamber 14 is pressurized. With the assistance of this pressurizing action, the liquid L in the liquid accommodating chamber 214 can be smoothly fed to the tip end of the liquid applicator member 215. Thus, the liquid fed to the tip end of the liquid applicator member 215 is brought into a state where it is allowed to be applied to a target surface, for example, a surface of a sheet of paper, and a surface of the skin of a human user. According to the liquid applying tool 210 of this embodiment, it is possible to prevent the generation of blurring of the applied liquid and/or the depletion of the liquid in the tip end of the liquid applicator member 215 which will be brought about by insufficient supply of the liquid L to the tip end of the liquid applicator member 215 from the liquid accommodating chamber 214. Moreover, only by the indispensable operation of removing the cap 120 from the outer container 112 which is performed at the time of the use of the liquid applying tool 210, the pressure in the liquid accommodating chamber 214 can be pressurized. Thus, it is possible to create the pressurizing action without any labor.

After the use of the liquid applying tool 210 is completed, the cap 120 is again attached to the liquid applying tool body 211. The attaching of the cap 120 to the liquid applying tool body 211 is carried out by putting the cap 120 on the front tubular portion 130a of the tubular shaft 130 of the outer container 112 and then causing the cap 120 to be rotated in a direction opposite to the predetermined direction. As the cap 120 is rotated in the direction opposite to the predetermined direction, the external thread portions 216c of the engagement protrusions 216b of the liquid accommodating tube 216 and the internal thread portion 150a of the cap body 150 of the cap 120 are threadedly engaged with one another, and the rear end edge of the cap 120 is abutted against the boundary step portion 130e between the front tubular portion 130a and tubular shaft body 130b of the tubular shaft 130. Thus, the cap 120 is perfectly attached to the liquid applying tool body 211. Moreover, as the external thread portions 216c of the engagement protrusions 216b of the liquid accommodating tube 216 and the internal thread portion 150a of the cap body 150 of the cap 120 are threadedly engaged with one another in this way, the cap 120 causes the liquid accommodating tube 216 to be pulled forward against the biasing action of the rearward biasing member 162, whereby the liquid storage container 213 is moved forward in the tubular shaft 130. By the forward movement of the liquid storage container 213, the compression member 140 is moved rearward relative to the liquid accommodating tube 216. As the compression member 140 is moved rearward, the seal member 142 is returned to the pressure relief portion 214a and the clearance is again created between the seal member 142 and the inner peripheral surface of the liquid accommodating tube 216. As a result, the pressure in the liquid accommodating chamber 214 is returned to the pressure equal to the atmospheric pressure (refer to FIG. 12).

Thus, every time the attaching/detaching operation of the cap 120 with respect to the outer container 112 is performed, releasing of the liquid accommodating chamber 214 from the pressurized state and pressurizing of the liquid accommodating chamber 214 can be repeated. Incidentally, in the third embodiment, the liquid storage container 213 is prevented from being rotated relative to the outer container 112 by engagement between the inner peripheral convex portions 130h (refer to FIGS. 9(b) and 9(c)), which are formed on the inner peripheral surfaces of the tubular shaft 130, and outer peripheral concave portions (not shown) which are formed on the outer peripheral surfaces of the liquid storage container 213. However, the mechanism for preventing the liquid storage container 213 from being rotated relative to the outer container 112 is not limited to such a mechanism and any suitable conventional mechanism for preventing the liquid storage container 213 from being rotated relative to the outer container 112 can be employed. For example, as the rotation preventing mechanism, there may be employed a rotation preventing mechanism which comprises axially extending groove portions formed in the inner peripheral surfaces of the tubular shaft body 130b of the tubular shaft 130, and convex portions formed on the outer peripheral surfaces of the liquid accommodating tube 216 and adapted to be engaged in the axially extending groove portions. Moreover, the cross-sectional shape of the inner peripheral surface of the tubular shaft 130 is formed into a polygonal shape, an elliptical shape, etc., and the cross-sectional shape of the outer peripheral surface of the liquid accommodating tube 216 is formed into a polygonal shape, an elliptical shape, etc., whereby the liquid storage container 213 can be prevented from being rotated with respect to the outer containers 112.

(Other Matters)

Although the liquid storage containers 13, 113, 213 of the first, second, and third embodiments are unexchangeably fixed to the outer containers 12, 112, the present invention is not limited to this, and the liquid storage containers 13, 113, 213 of the first, second, and third embodiments may be configured so as to be exchangeable with respect to the outer containers 12, 112. For example, the liquid storage container may be configured as a refill-type liquid storage container which is exchangeably attached to a fixing member that is unexchangeably provided at the outer container 12 or 112. In this case, in order that the refill-type liquid storage container can be easily removed from the outer container 12 or 112, the tubular shaft 30 or 130 of the outer container is preferably assembled from plural detachable members.

The present invention can be applied to the following articles (1) to (4) as well as writing instruments such as ballpoint pens and marking pens which include the liquid storage containers 13, 113, 213 having ink as the liquid L to be applied to target surfaces.

(1) A correcting device including the liquid storage container 13, 113 or 213 which has correction liquid as the liquid L to be applied to a target surface;

(2) A cosmetics applicator including the liquid storage container 13, 113 or 213 which has liquid cosmetic as the liquid L to be applied to a target surface;

(3) A medicine applicator including the liquid storage container 13, 113 or 213 which has medical liquid as the liquid L to be applied to a target surface; and (4) A liquid adhesive applicator including the liquid storage container 13, 113 or 213 which has liquid adhesive as the liquid L to be applied to a target surface.

REFERENCE SIGNS LIST 10, 110, 210: Liquid applying tool
11, 111, 211: Liquid applying tool body
12, 112: Outer container
13, 113, 213: Liquid storage container 14, 114, 214: Liquid accommodating chamber
14a, 114a, 214a: Pressure relief portion
14b: Tapered inner surface
15, 115, 215: Liquid applicator member
15a, 115a: Tip end
16, 116, 216: Liquid accommodating tube
16a: Annular rib
116a, 216a: Step portion
216b: Engagement protrusion
216c: External thread portion
20, 120: Cap
30, 130: Tubular shaft
30a, 130a: Front tubular portion
30b, 130b: Tubular shaft body
30c, 130c: Tip end opening
30d: Engagement portion
130d: Step portion
30e, 130e: Boundary step portion
30f, 130f: Side hole
30g: External thread portion
30h, 130h: Inner peripheral convex portion
32, 132: Tail plug
40, 140: Compression member
40a, 140a: Annular concave portion
40b: Elastic piece
140b: Flange portion
40c: Protrusion
140c: Engaging concave portion
140d: Engagement portion
42, 142: Seal member
50, 150: Cap body
50a, 150a: Internal thread portion
50b: Inner diameter-increased step portion
52, 152: Inner cap
54, 154: Receptacle portion
60, 160: Power transmitting member
60a, 160a: Engagement piece
60b: Protruding portion
160b: External thread portion
60c. 160c: Outer peripheral concave portion
60d, 160d: Annular convex portion
62: Forward biasing member (Spring)
162: Rearward biasing member (Spring)
L: Liquid

What is claimed is:

1. A liquid applying tool comprising:
a liquid storage container having liquid stored therein and a liquid applicator member provided at a tip end portion thereof for applying the liquid;
an outer container;
the liquid storage container being housed in the outer container with at least a tip end of the liquid applicator member thereof being exposed to an outside of the outer container;
a cap removably attached to a tip end portion of the outer container so as to cover the tip end of the liquid applicator member;
a compression member arranged at a rear end portion of the liquid storage container in the outer container; and
a power transmitting member configured to be reciprocation-moved in an axial direction in the outer container according to attaching/detaching of the cap, whereby one of the compression member and the liquid storage container is reciprocation-moved relative to the other of the compression member and the liquid storage container in the axial direction, wherein the liquid storage container has a pressure relief portion allowing air to pass therethrough to return a chamber pressure equal to the atmospheric pressure.

2. The liquid applying tool according to claim 1, wherein the power transmitting member is adapted to be moved forward in the axial direction in the outer container according to detaching of the cap from the outer container, and the compression member is adapted to be moved forward relative to the liquid storage container in the axial direction according to the forward movement of the power transmitting member, the power transmitting member is adapted to be moved rearward in the axial direction in the outer container according to attaching of the cap to the outer container, and the compression member is adapted to be moved rearward relative to the liquid storage container in the axial direction according to the rearward movement of the power transmitting member.

3. The liquid applying tool according to claim 2, including a forward biasing member provided in the outer container for causing the compression member to be biased forward in the axial direction.

4. The liquid applying tool according to claim 1, wherein the power transmitting member is arranged between an inner peripheral surface of the outer container and an outer peripheral surface of the liquid storage container.

5. A liquid applying tool comprising:
a liquid storage container having liquid stored therein and a liquid applicator member provided at a tip end portion thereof for applying the liquid;
an outer container;
the liquid storage container being housed in the outer container with at least a tip end of the liquid applicator member thereof being exposed to an outside of the outer container;
a cap removably attached to a tip end portion of the outer container so as to cover the tip end of the liquid applicator member;
a compression member arranged at a rear end portion of the liquid storage container in the outer container; and
a power transmitting member configured to be reciprocation-moved in an axial direction in the outer container according to attaching/detaching of the cap, whereby one of the compression member and the liquid storage container is reciprocation-moved relative to the other of the compression member and the liquid storage container in the axial direction,
wherein the power transmitting member is adapted to be moved rearward in the axial direction in the outer container according to detaching of the cap from the outer container, and the liquid storage container is adapted to be moved rearward relative to the compression member in the axial direction according to the rearward movement of the power transmitting member, the power transmitting member is adapted to be moved forward in the axial direction in the outer container according to attaching of the cap to the outer container, and the liquid storage container is adapted to be moved forward relative to the compression member in the axial direction according to the forward movement of the power transmitting member.

6. The liquid applying tool according to claim 5, including a rearward biasing member provided in the outer container for causing the liquid storage container to be biased rearward in the axial direction.

7. The liquid applying tool according to claim 5, the liquid storage container is formed integrally with the power transmitting member.

\* \* \* \* \*